(12) United States Patent
Park et al.

(10) Patent No.: US 7,970,245 B2
(45) Date of Patent: Jun. 28, 2011

(54) OPTICAL BIOSENSOR USING SPR PHENOMENON

(75) Inventors: Kwang No Park, Seoul (KR); Kyung Shik Lee, Seoul (KR); Hyun Soo Jang, Seoul (KR); Byeong Cheol Min, Seoul (KR)

(73) Assignee: Sungkyunkwan University Foundation for Corporate Collaboration, Gyeonggi-Do (KR)

( * ) Notice: Subject to any disclaimer, the term of this patent is extended or adjusted under 35 U.S.C. 154(b) by 291 days.

(21) Appl. No.: 12/032,822

(22) Filed: Feb. 18, 2008

(65) Prior Publication Data
US 2009/0059211 A1 Mar. 5, 2009

(30) Foreign Application Priority Data
Jul. 18, 2007 (KR) .................. 10-2007-0071784

(51) Int. Cl.
G02F 1/295 (2006.01)
G02B 6/00 (2006.01)
G02B 6/34 (2006.01)

(52) U.S. Cl. .................. 385/37; 385/4; 385/12; 385/27

(58) Field of Classification Search .............. 356/39–44; 385/12–13, 15, 31, 37, 123, 126, 127, 141, 385/4, 27, 28; 250/227.14, 227.18, 227.23
See application file for complete search history.

(56) References Cited

U.S. PATENT DOCUMENTS

| | | | |
|---|---|---|---|
| 4,749,248 A * | 6/1988 | Aberson et al. | 385/37 |
| 5,015,052 A * | 5/1991 | Ridgway et al. | 385/2 |
| 5,042,897 A * | 8/1991 | Meltz et al. | 385/37 |
| 5,061,032 A * | 10/1991 | Meltz et al. | 385/37 |
| 5,732,170 A * | 3/1998 | Okude et al. | 385/27 |
| 5,864,641 A * | 1/1999 | Murphy et al. | 385/12 |
| 6,021,240 A * | 2/2000 | Murphy et al. | 385/37 |
| 6,058,226 A * | 5/2000 | Starodubov | 385/12 |
| 6,104,851 A * | 8/2000 | Mahgerefteh | 385/37 |
| 6,282,338 B1 * | 8/2001 | Egalon | 385/28 |
| 6,343,168 B1 * | 1/2002 | Murphy et al. | 385/37 |
| 6,411,755 B1 * | 6/2002 | Erdogan | 385/28 |
| 6,519,388 B1 * | 2/2003 | Fernald et al. | 385/37 |
| 6,529,671 B2 * | 3/2003 | MacDougall | 385/137 |
| 6,556,735 B1 * | 4/2003 | Kato | 385/14 |
| 6,697,541 B1 * | 2/2004 | Chen et al. | 385/4 |
| 6,845,194 B2 * | 1/2005 | Ramachandran | 385/37 |
| 6,885,792 B2 * | 4/2005 | Eggleton et al. | 385/37 |
| 6,917,734 B2 * | 7/2005 | Pfeiffer | 385/27 |
| 7,336,861 B2 * | 2/2008 | Wang et al. | 385/12 |
| 7,340,119 B1 * | 3/2008 | Xu et al. | 385/12 |

FOREIGN PATENT DOCUMENTS

JP 2000-009495 1/2000
KR 10-0405898 11/2003

OTHER PUBLICATIONS

Office Action for Korean Patent Application No. 10-2007-0071784 dated Nov. 25, 2008.

* cited by examiner

*Primary Examiner* — Sang Nguyen
(74) *Attorney, Agent, or Firm* — RatnerPrestia

(57) ABSTRACT

An optical biosensor using a surface plasmon resonance phenomenon includes an input optical waveguide including a first optical mode converting unit for converting a core mode to a cladding mode; and an optical sensing unit for allowing a specific wavelength among wavelengths constituting the converted cladding mode to be lost according to density of biomaterial. The optical biosensor can accurately measure density of bio-material by using an optical signal.

12 Claims, 8 Drawing Sheets

OPTICAL BIOSENSOR USING SPR PHENOMENON

FIELD OF THE INVENTION

The present invention relates to an optical biosensor based on a surface plasmon resonance (SPR) phenomenon, and more particularly to an optical biosensor detecting density of bio-material by measuring an optical signal change at a specific wavelength due to mode coupling among waveguide modes and surface plasmon modes.

BACKGROUND

FIG. 1 illustrates a conventional biosensor based on an electronic circuit. The conventional biosensor based on an electronic circuit can measure a result obtained by converting an amount of electric or magnetic change of bio-material to be detected to current or voltage so as to detect density and a characteristic of the bio-material. For example, when density of bio-material to be measured is changed, the resistance value of the bio-material is also changed.

Accordingly, current and voltage through the bio-material are changed so that, by using this changed value, change of density of the bio-material can be measured.

It is possible to determine if any disease exists by measuring change of an amount of blood sugar or change of density bio-material including material causing various kinds of diseases.

FIG. 2 is a view illustrating a conventional optical biosensor using a SPR phenomenon, in which the optical biosensor has undergone an etching process, and FIG. 3 is a view illustrating a conventional optical biosensor using a SPR phenomenon, in which the optical biosensor has undergone a polishing process.

A surface Plasmon Resonance (SPR) phenomenon is used in a method for measuring density of bio-material to be detected by using an optical phenomenon. So as to measure density of a specific bio-material by using an optical technique, first, a bio-material detecting part reacting to a specific bio-material has to be attached to the exterior of an optical waveguide. At this time, a typical bio-material detecting part may not be attached to an optical waveguide based on silica. Meanwhile, the bio-material detecting part has its own property allowing attachment to metal such as Au, and an optical waveguide based on silica can be easily coated with metal. Therefore, a metallic layer, which can be attached to a bio-material detecting layer as well as an optical waveguide based on silica, is inserted between the optical waveguide and the bio-material detecting layer so that the bio-material detecting layer can be combined with the optical waveguide. Therefore, a biosensor is implemented. In a case where bio-material is added to the above structured biosensor, reaction occurs in the bio-material detecting layer. At this time, an amount of physical reaction is changed according to density of bio-material. This finally causes change of refractive index. Due to such a change of refractive index in the bio-material detecting layer attached to the exterior of the metallic layer, a phenomenon that only a signal of a specific wavelength, among optical signals propagating through the optical waveguide, couples to the outside of the biosensor and disappears through the surface plasmon resonance (SPR).

A method for etching or polishing a cladding area of an optical waveguide is performed to a conventional optical biosensor so as to generate an SPR phenomenon. In case of a conventional optical biosensor, to generate the SPR phenomenon, a distance between a core area through which an optical signal propagates and an outer sensing area at which a bio-material reacts needs to be short within several micrometers. In order to achieve this, a process for etching or polishing a cladding area is a necessary process in manufacturing a sensing part of the conventional optical biosensor.

Therefore, there will be a problem in that manufacturing costs increase due to such a process for etching or polishing in manufacturing an optical biosensor.

Also, the complicate manufacturing process makes it difficult to realize the mass production of the biosensor.

SUMMARY OF THE INVENTION

Accordingly, the present invention has been made to solve the above-mentioned problems occurring in the prior art, and the present invention provides an optical biosensor which can accurately measure density of a bio-material by using an optical signal.

Also, the present invention provides an optical biosensor manufactured without undergoing an etching process or a polishing process.

Also, the present invention provides an optical biosensor having a structure allowing a sensing part to be easily displaced.

Another object of the present invention will be easily understood through illustration of following embodiments.

In accordance with an aspect of the present invention, there is provided an optical biosensor, which may include: an input optical waveguide including a first optical mode converting unit for converting a core mode to a cladding mode; and an optical sensing unit for allowing a specific range of wavelength among the overall wavelengths constituting the spectrum of the converted cladding mode to be diminished according to density of bio-material.

Preferably, the optical sensing unit be able to allow an optical signal at a specific range of wavelength to lose its power through the cladding mode-to-surface plasmon mode coupling process, according to the density of bio-material.

The optical biosensor may further include an output optical waveguide including a second optical mode converting unit for converting the cladding mode to a core mode in the specific range of wavelength, within which an optical signal power is diminished.

Therefore, the optical signal power contained in the waveguide mode such as core mode and the cladding mode at specific range of wavelength will be changed through the SPR phenomenon in the optical sensing unit.

The optical sensing unit may include the optical sensing unit includes a bio-material sensing unit at an exterior of the optical waveguide, the bio-material sensing unit being coated with indicating material reacting to a metallic layer and a specific bio-material.

The optical sensing unit may include the optical sensing unit includes a bio-material sensing unit at an exterior of the optical waveguide, the bio-material sensing unit being coated with a metallic layer, buffer layer and a specific bio-material.

The first and second optical mode converting units may be in a form of waveguide grating such as optical fiber grating including long period fiber grating, chirped grating, sampled grating. The mode converting units may also be in a form of waveguide such as corrugated waveguide, tapered waveguide.

The method for measuring density of bio-material by using an optical biosensor, which may include the steps of: converting, by a first optical mode converting unit, a core mode to a cladding mode so as to output the cladding mode; diminishing, by an optical sensing unit, a specific range of wavelength among the overall wavelengths constituting the spectrum of the outputted cladding mode according to density of bio-material; and analyzing, by an optical signal detector, the diminished specific range of wavelength so as to detect a density of the bio-material.

The method for measuring density of bio-material may further include the step of converting the cladding mode where the specific range of wavelength is diminished to a core mode so as to output the core mode by the second optical mode converting unit.

The core mode can be either fundamental mode or higher order mode depending on the core size of the waveguide. For example, for a single mode waveguide, the core mode is fundamental mode.

Similarly, the first and second optical mode converting units may be in a form of a grating and a waveguide.

An optical biosensor according to the present invention has an effect of accurately measuring density of a bio-material by using an optical signal.

Also, the present invention has an effect of providing an optical biosensor manufactured without undergoing an etching process or a polishing process.

Also the present invention has an effect of providing an optical biosensor having a structure allowing a sensing part to be easily displaced.

BRIEF DESCRIPTION OF THE DRAWINGS

The above and other objects, features and advantages of the present invention will be more apparent from the following detailed description taken in conjunction with the accompanying drawings, in which.

DETAILED DESCRIPTION OF THE EXEMPLARY EMBODIMENTS

Figure 1:
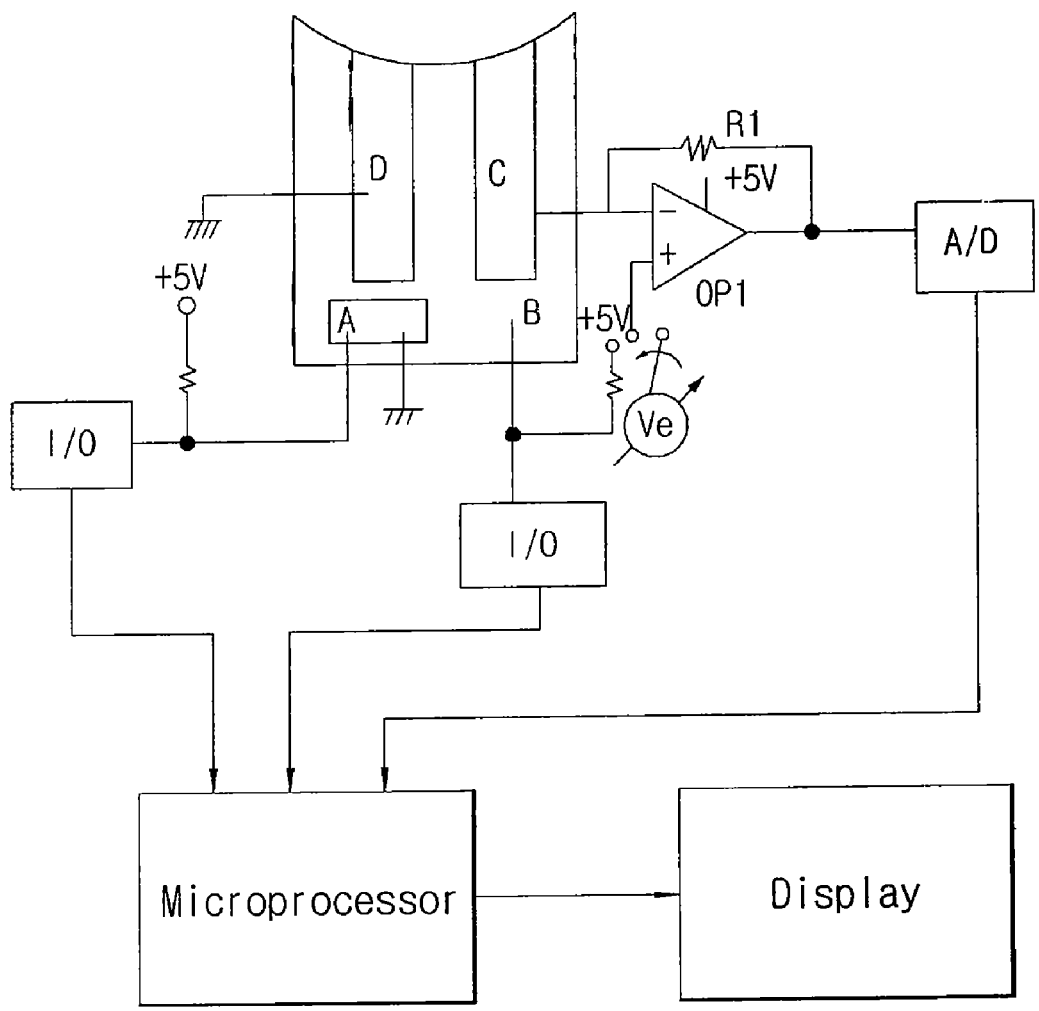
FIG. 1 is a view illustrating a conventional biosensor based on an electronic circuit.
Figure 2:
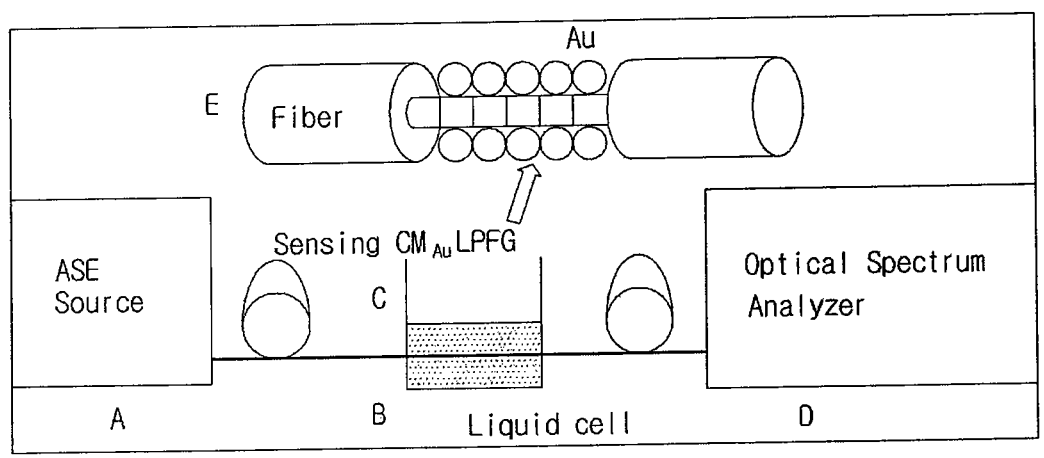
FIG. 2 is a view illustrating a conventional optical biosensor using a SPR phenomenon, to which an etching process is applied.
Figure 3:
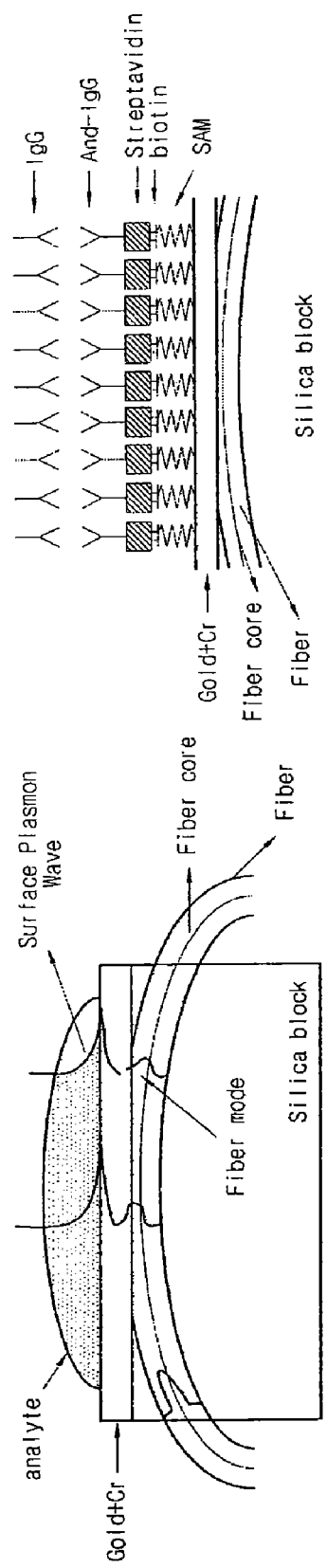
FIG. 3 is a view illustrating a conventional optical biosensor based on a SPR phenomenon, to which a polishing process is applied.

The present invention may be modified and has various embodiments so that specific embodiments will be described with reference to the accompanying drawings. However, the scope of the invention is not to be limited by these embodiments, and it will be understood by those skilled in the art that modifications, equivalents and substitutions may be made therein without departing from the spirit and scope of the invention. The same reference numerals are used to designate the same or similar components in described each drawing.

Although terms such as 'The first', 'the second', 'A', and 'B' can be used for describing various components, the components may not limited by the terms. The terms are used only for distinguishing one component from another component. For example, a first component may be designated as a second component, and similarly, the second component may be designated as the second component. The use of the term of 'and/or' means that combination of a plurality of related and described items or one items among a plurality of related and described items is included.

When it is mentioned that a certain component is "coupled with" or "connected with" another component, it may be understood that another component can exist between the two components although the component can be directly coupled or connected with the another component. Meanwhile, when it is mentioned that a certain component is "directly coupled with" or "directly connected with" another component, it has to be understood that another component does not exist between the two components.

Terms used in the present invention are used for describing a specific embodiment, and do not limit the present invention. Singular expressions include plural expressions which do not have any obviously different meaning in view of a context. In the present invention, it is understood that terms such as "include" or "have", etc. are used for designating existence of characteristics, numbers, steps, operations, components, parts, or combination of these, and not for excluding the possibility of existence or addition of at least one characteristic, number, step, operation, component, part, or combination of these.

As far as terms not designated as being a different meanings, all terms including technical or scientific terms, which are used herein, have the same meaning as those generally understood by those skilled in the art. It has to be understood that terms defined by a typical dictionary have meanings corresponding to a related art. Also, as long as they are not obviously defined in the present invention, they may be not understood as idealistic meanings or excessively formal meanings.

Hereinafter, exemplary embodiments of the present invention will be described in detail with reference to the accompanying drawings. So as to help through understanding in describing the present invention, the same reference numerals are used to designate the same means regardless of numeric references.

Embodiment

Figure 4:
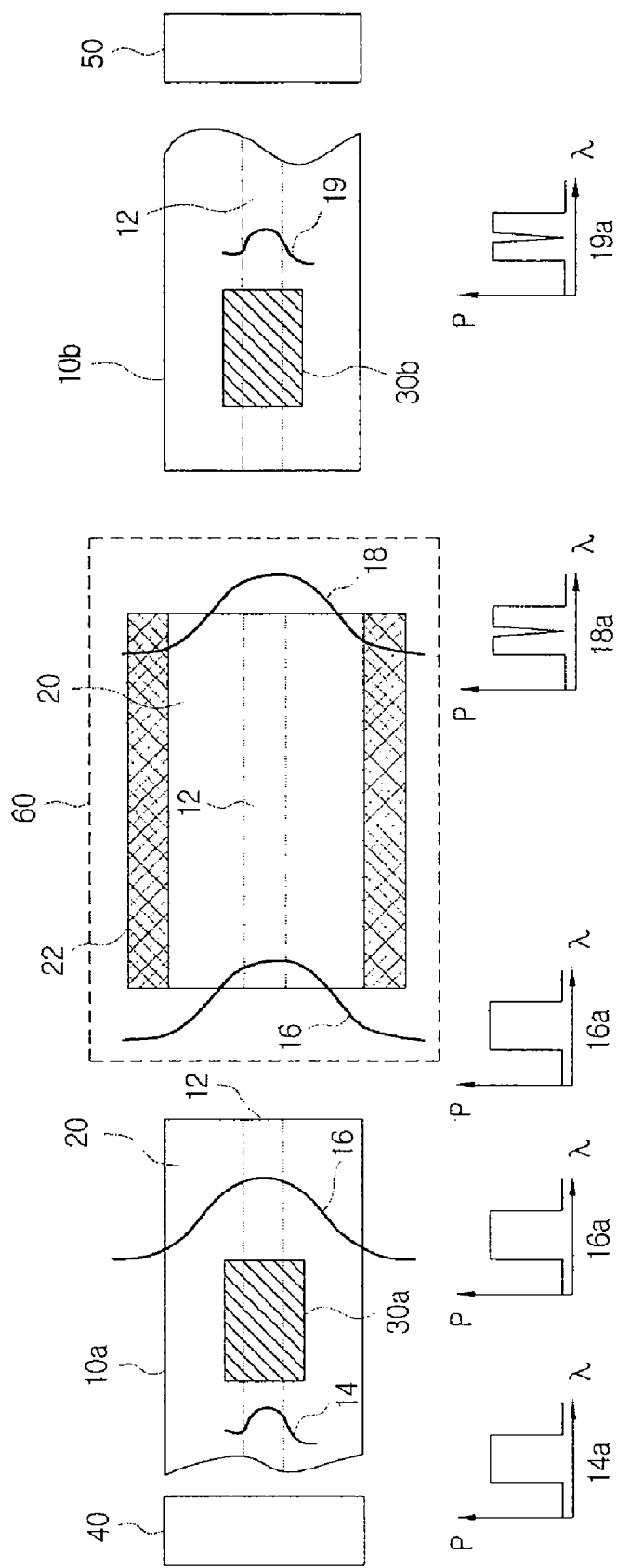
FIG. 4 is a view illustrating a construction of an optical biosensor using a SPR phenomenon according to an embodiment of the present invention.
Figure 5:
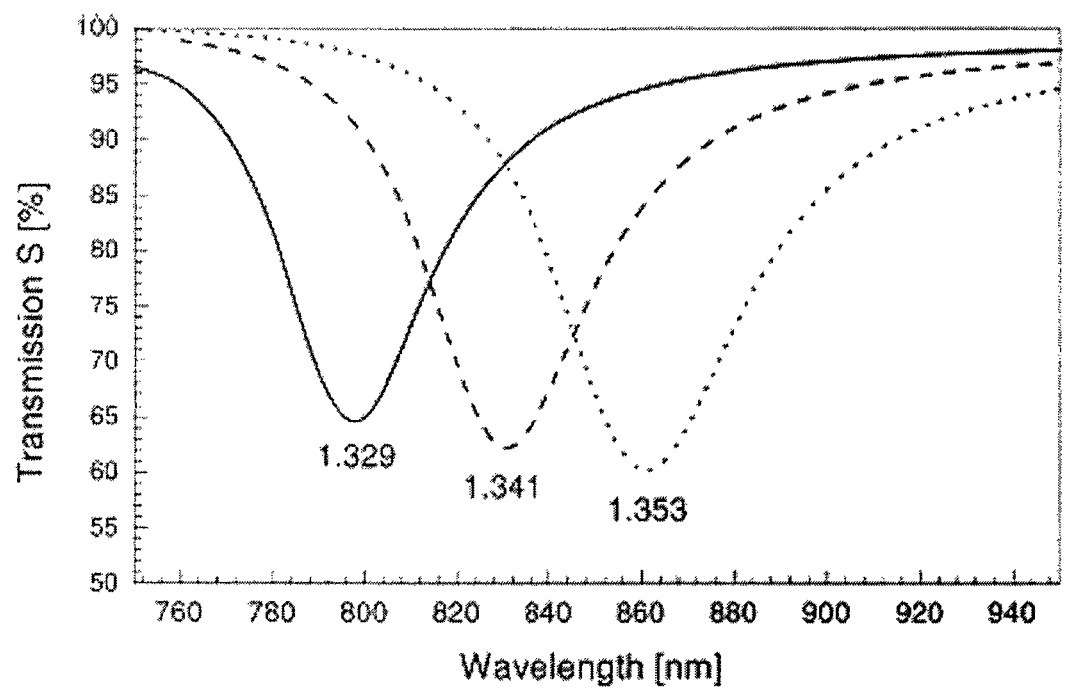
FIG. 5 is a view illustrating an optical spectrum of a cladding mode outputted from an optical sensing unit according to an embodiment of the present invention.
Figure 6:
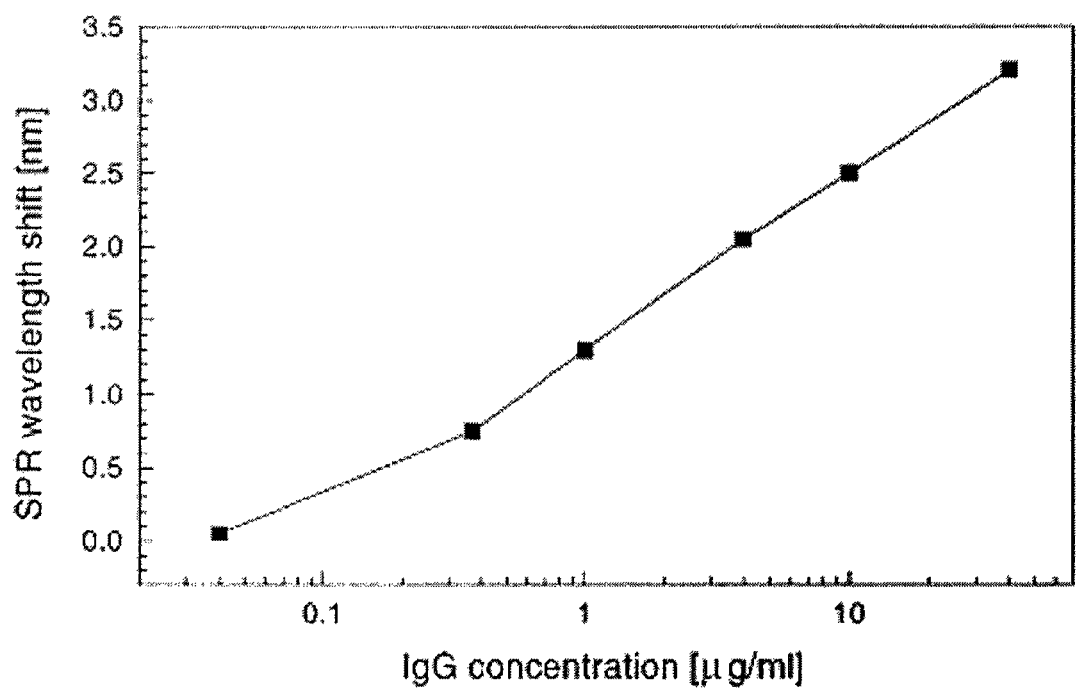
FIG. 6 is a graph illustrating change of a wavelength to be diminished depending on density of bio-material according to an embodiment of the present invention.

FIG. 4 is a view illustrating a construction of an optical biosensor using a SPR phenomenon according to an embodiment of the present invention, FIG. 5 is a view illustrating an optical spectrum of a cladding mode outputted from an optical sensing unit according to an embodiment of the present invention, and FIG. 6 is a graph illustrating the shifts of wavelength where the mode coupling between the cladding mode and the surface plasmon mode occurs, resulting in a substantial signal power drop, with respect to the density of bio-material (i.e., here, IgG concentration) according to an embodiment of the present invention.

With reference to FIG. 4, an optical sensor according to the present invention may include an input optical waveguide (i.e. an optical fiber or planar waveguide) 10a, an optical sensing unit 60, and an output optical waveguide 10b. Light 14 or an optical signal 14a, which has been emitted from an optical source 40 and has been inputted into the input optical waveguide 10a, can pass through the optical sensing unit 60 and the output optical waveguide 10b so as to be inputted into an optical signal detector 50. At this time, an optical signal 19 and 19a are received by the optical signal detector 50. Note that the optical signal power drops significantly through the mode coupling or the SPR at wavelength determined by the density of bio-material. This signal change in terms of power level and the wavelength shift can be analyzed so as to deduce (or measure, detect) the density of the corresponding bio-material.

An optical waveguide (an optical fiber) used in the present invention, which is included in the input optical waveguide 10a, the optical sensing unit 60, and the output optical waveguide 10b, includes a core area 12 and a cladding area 20. At this time, light or an optical signal guiding (or propagating) through the core area 12 refers to a core mode, and light or an optical signal propagating through the cladding area 20 refers to a cladding mode.

The input optical waveguide 10a includes a first optical mode converting unit 30a for converting a core mode 14 and 14a to a cladding mode 16 and 16a. Herein, according to an embodiment of the present invention, the first optical mode converting unit 30a may be based on a waveguide grating such as long period fiber grating, chirped grating and sampled grating, and in addition, any means, which can convert the core mode 14 and 14a to the cladding mode 16 and 16a, may be used without any limitation. The waveguide grating can be manufactured in such a manner that an effective index of the core 12 of the optical waveguide is periodically modulated with a period between several tens nanometers and several thousands namometers. The waveguide grating including the long period fiber grating can be manufactured by using the phase mask method and the holographic method that use a UV beam to expose the optical waveguide to an interference pattern of the UV beam until a periodic index perturbation along the waveguide occurs. Also, the long period fiber grating can be manufactured in such a manner that pressure is applied to the optical waveguide by using a mold capable of periodically exerting pressure from an outside so as to change an effective index of the core area 12. Various well known etching techniques can also apply to form the waveguide grating. In general, light or an optical signal progressing through the optical waveguide has a characteristic that it can propagate only through an area designated as a core area 12. If the above described long period fiber grating is implemented in the core area 12 through which light or an optical signal propagates, the core mode 14 and 14a can be converted to the cladding mode 16 and 16a under the phase matching condition. Particularly, light or an optical signal, which propagates through the core area 12 is coupled to the cladding mode 16 by the long period fiber grating. The optical sensing unit 60 includes a bio-material sensing unit 22 coated with indicating material reacting to a metallic layer disposed outside the optical waveguide and a specific bio-material. At this time, in the optical sensing unit 60, the cladding mode 16 and 16a at a specific wavelength has a SPR phenomenon according to density of bio-material to be detected. Particularly, light or an optical signal of a specific wavelength between the optical waveguide and the metallic layer is optically combined and coupled. As a result, the optical signal at the specific wavelength where an SPR phenomenon has occurred drops substantially outside the optical sensing unit 60 so that a cladding mode 18 and 18a outputted from the optical sensing unit 60 is in a state where a specific wavelength has been appeared to be missing in comparison with the cladding mode 16 and 16a inputted from the input optical waveguide 10a. At this time, a wavelength appeared missing, among wavelengths constituting each cladding mode, may be changed according to the density of bio-material. By using this fact, when a wavelength, which has been lost due to an SPR phenomenon, is measured so as to be inversely analyzed, the density of corresponding bio-material can be detected. FIG. 5 shows several examples of optical spectrums of a cladding mode outputted from the optical sensing unit 60, indicating the specific wavelengths are about 795 nm, 830 nm and 865 nm. FIG. 6 shows the successive change of the wavelength at which the optical signal drops according to density of bio-material, and by using this change, the density of the corresponding bio-material can be determined. In FIG. 5, a horizontal axis is a wavelength, and the vertical axis is intensity of an optical signal propagated from the sensing unit. The numbers 1.329, 1.341, and 1.353 in FIG. 5 show the change of refractive index according to the change of density of bio-material. Therefore, as shown in FIG. 5, a wavelength (795 nm, 830 nm, and 865 nm) of a wavelength reacting according to change of density of bio-material is changed. In FIG. 6, a horizontal axis is density of bio-material, and a vertical axial is the degree of change of a reacting wavelength according to change of density of bio-material. As shown in FIG. 6, a wavelength reacting in the optical biosensor is changed according to change of density of bio-material. Particularly, density of bio-material can be detected by measuring the degree of change of a wavelength reacting in the optical biosensor.

The output optical waveguide 10b includes a second optical mode converting unit 30b for converting the cladding mode 18 and 18a to the core mode 19 and 19a. Herein, according to an embodiment of the present invention, the second optical mode converting unit 30b may be made with a long period waveguide grating or a corrugated waveguide or tapered waveguide just like the first optical mode converting unit, and in addition to the long period waveguide grating, any means which can convert the cladding mode 18 and 18a to the core mode 19 and 19a can be used without any limitation. The optical signal detector 50 performs a function for analyzing light and an optical signal 19 and 19a outputted from the output optical waveguide 10b so as to detect the density of the bio-material. At this time, if a wavelength, which has been lost due to a SPR phenomenon, is measured so as to be inversely analyzed, density of bio-material can be detected. At this time, an apparatus, such as an optical power detector for detecting light, an optical signal, or an optical spectrum analyzer (OSA), may be used as the optical signal detector 50. The optical spectrum analyzer can be replaced by a CCD array (or photo diode array) in combination with a dispersing element such as prism and grating for analyzing the spectrum of the optical signal.

According to another embodiment of the present invention, the optical signal detector 50 can perform a function for detecting the density of bio-material by analyzing light 50 or the optical signal 18 and 18a outputted from the optical sensing unit 60 10b. In this case, the output optical waveguide 10b is not an essential element of the present invention.

Figure 7:
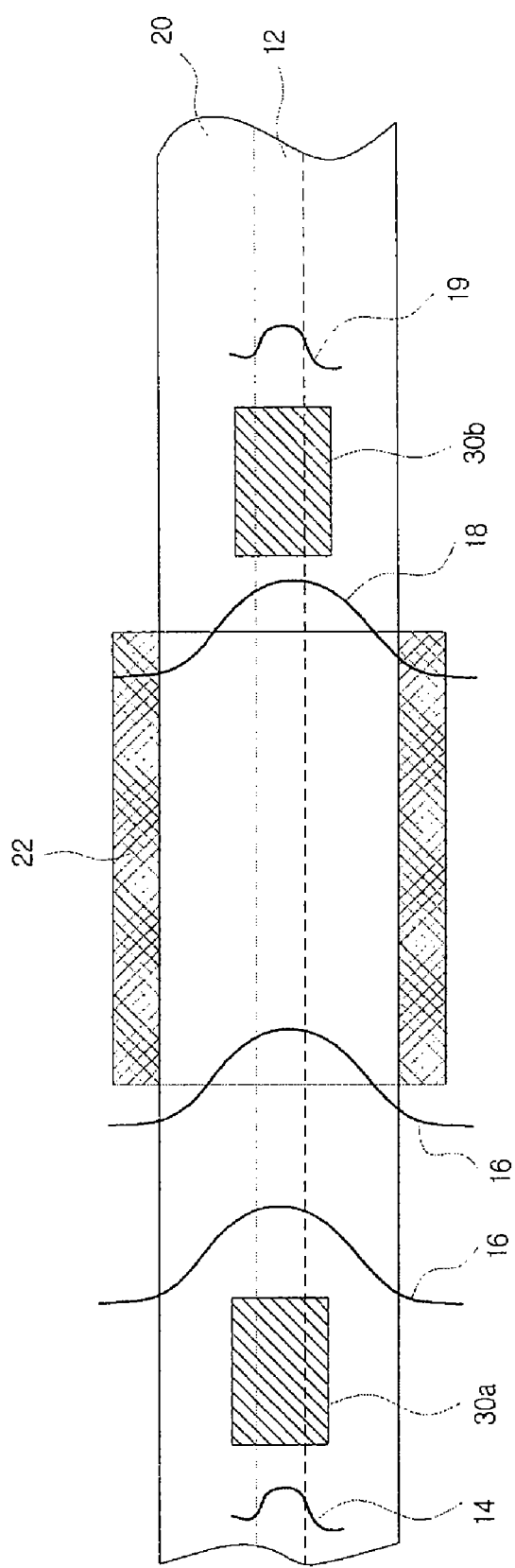
FIG. 7 is a view illustrating an optical biosensor based on a SPR phenomenon according to another embodiment of the present invention.

FIG. 7 is a view illustrating the structure of an optical biosensor using a SPR phenomenon according to another embodiment of the present invention.

As shown in FIG. 7, the optical biosensor according to the present invention may include a first optical mode converting unit 30a, a bio material sensing unit 22, and a second optical mode converting unit 30b in an optical waveguide (an optical fiber), which is an integral one. Particularly, an input optical waveguide 10a, an optical sensing unit 60, and an output optical waveguide 10b can share the same optical waveguide (an optical fiber or a planar waveguide) so as to be provided in an integral shape. An operational characteristic of the biosensor shown in FIG. 7 is the same as the biosensor shown in FIG. 4. Therefore, the detailed description of the operational characteristic will be omitted.

Figure 8:
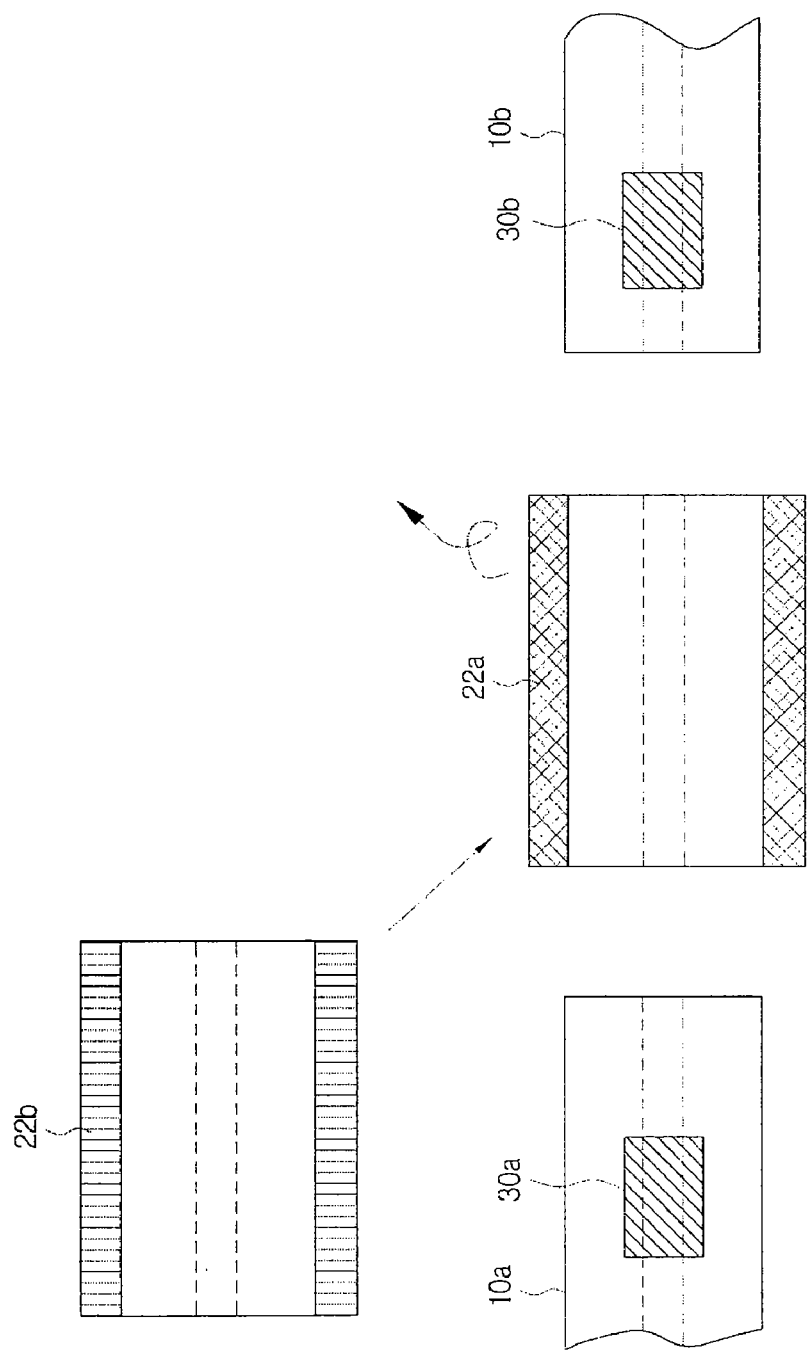
FIG. 8 is a view illustrating a method for providing an optical sensing unit which can detect density of bio-material different from a conventional material according to an embodiment.

FIG. 8 is a view illustrating a method for providing an optical sensing unit which can detect density of bio-material different from a conventional material according to an embodiment. As shown in FIG. 8, an optical sensing unit 60 may be provided, which can detect various pieces of bio-material in such a manner that a bio material sensing unit 22 included in an optical sensing unit 60 is coated with indicating material 22a and 22b, which reacts to pieces of bio-material different from each other. At this time, the input optical waveguide 10a and the output optical waveguide 10b, which are described above, are used, and the optical sensing unit 60 coated with the above described indicating material 22a is displaced with (replaced by?) an optical sensing unit 60 coated with new indicating material 22b so that an optical biosensor, which can detect various pieces of bio-material, can be usefully provided. Indicating material is generally composed of metal layer and immobilized ligand. One immobilized ligand used in the indicator material interacts with specific bio-material. And this interaction causes change of optical property in the bio sensing unit 60. So an optical sensing unit 60 can detect various pieces of bio-material by changing the immobilized ligand used in the indicator material.

Although an exemplary embodiment of the present invention has been described for illustrative purposes, those skilled in the art will appreciate that various modifications, additions and substitutions are possible, without departing from the scope and spirit of the invention as disclosed in the accompanying claims.

What is claimed is:

1. An optical biosensor comprising:
   an input optical waveguide including a first optical mode converting unit for converting a core mode to a cladding mode; and
   an optical sensing unit disposed linear to the first optical mode converting unit and coupled to the input optical waveguide, the optical sensing unit including a waveguide for receiving the converted cladding mode; and
   a bio-material sensing unit at an exterior of the waveguide, the bio-material sensing unit including a metallic layer disposed on an exterior of a cladding of the waveguide and an indicating material which reacts to the metallic layer and the bio-material, the bio-material sensing unit allowing a specific range of wavelengths among overall wavelengths constituting a spectrum of the converted cladding mode to be diminished according to a density of a bio-material, the specific range of wavelengths being diminished is responsive to a surface plasmon resonance (SPR) phenomenon between the metallic layer and the cladding.

2. The optical biosensor as claimed in claim 1, further comprising an output optical waveguide including a second optical mode converting unit for converting the cladding mode to a core mode in the specific range of wavelengths, within which an optical signal power is diminished.

3. The optical biosensor as claimed in claim 2, wherein the first and second optical mode converting units are made of a waveguide grating.

4. The optical biosensor as claimed in claim 2, wherein the first and second optical mode converting units are made of a long period fiber grating.

5. The optical biosensor as claimed in claim 1, wherein the bio-material sensing unit includes a buffer layer.

6. The optical biosensor as claimed in claim 1, wherein the first optical mode converting unit is made of a tapered waveguide.

7. The optical biosensor as claimed in claim 2, wherein the second optical mode converting unit is made of a tapered waveguide.

8. The optical biosensor as claimed in claim 1, wherein the optical sensing unit is detachably coupled to the input optical waveguide.

9. A method for measuring a density of a bio-material by using an optical biosensor, comprising the steps of:
   converting, by a first optical mode converting unit, a core mode to a cladding mode so as to output the cladding mode;
   diminishing, by an optical sensing unit, a specific range of wavelengths among overall wavelengths constituting a spectrum of the outputted cladding mode according to a density of a bio-material; and
   analyzing, by an optical signal detector, the diminished specific range of wavelengths so as to detect a density of the bio-material,
   wherein the optical sensing unit includes a waveguide for receiving the outputted cladding mode and a bio-material sensing unit at an exterior of the waveguide for diminishing the specific range of wavelengths,
   wherein the bio-material sensing unit includes a metallic layer disposed on an exterior of a cladding of the waveguide and an indicating material which reacts to the metallic layer and the bio-material, the specific range of wavelengths being diminished responsive to a surface plasmon resonance (SPR) phenomenon between the metallic layer and the cladding, and
   wherein the optical sensing unit is disposed linear to the first optical mode converting unit and is coupled to the first optical mode converting unit.

10. A method for measuring density of bio-material as claimed in claim 9, further comprising the step of converting the cladding mode where the specific range of wavelengths is diminished to a core mode so as to output the core mode by a second optical mode converting unit.

11. The method for measuring density of bio-material as claimed in claim 10, wherein the first and second optical mode converting units are based on a long period fiber grating.

12. The method for measuring a density of a bio-material as claimed in claim 9, further comprising detachably coupling the optical sensing unit to the first optical mode converting unit.

* * * * *